US00H002251H

(19) United States

(12) Statutory Invention Registration

Malmstrom et al.

(10) Reg. No.: US H2251 H

(43) Published: Jan. 4, 2011

(54) METHOD OF PREPARING MULTIPLE DOSES OF A PHARMACEUTICAL SOLUTION FROM A SINGLE-DOSE

(75) Inventors: Robert A. Malmstrom, San Leandro, CA (US); Joy L. Meier, Martinez, CA (US); Jannet M. Carmichael, Reno, NV (US)

(73) Assignee: The United States of America as represented by the United States Department of Veterans Affairs, Washington, DC (US)

(21) Appl. No.: 12/453,488

(22) Filed: May 12, 2009

(51) Int. Cl.
*B65B 3/04* (2006.01)

(52) U.S. Cl. ..... 141/2

(58) Field of Classification Search ..... 141/2; 604/403; 206/571
See application file for complete search history.

(56) References Cited

U.S. PATENT DOCUMENTS 6,073,759 A * 6/2000 Lamborne et al. ..... 604/521
6,494,314 B1 * 12/2002 Lamborne et al. ..... 604/521
7,744,580 B2 * 6/2010 Reboul ..... 604/403

* cited by examiner

*Primary Examiner*—Dan Pihulic
(74) *Attorney, Agent, or Firm*—Dinesh Agarwal, P.C.

(57) ABSTRACT

A method of preparing multiple doses of a pharmaceutical solution, such as ranibizumab, from a single-dose container, includes providing a sterile enclosed area with a plurality of unused sterile syringes, a decapper, and a plurality of sterile bags, opening a single-use container of a pharmaceutical solution in the enclosed area, withdrawing a first portion of the pharmaceutical solution using one of the sterile syringes, withdrawing a second portion of the pharmaceutical solution using a second of the sterile syringes, repeating the previous step for the remaining pharmaceutical solution using the remaining sterile syringes, and placing the sterile syringes containing portions of the pharmaceutical solution individually in the sterile bags.

17 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD OF PREPARING MULTIPLE DOSES OF A PHARMACEUTICAL SOLUTION FROM A SINGLE-DOSE

FIELD AND BACKGROUND OF THE INVENTION

The present invention is generally directed to a method of preparing multiple individual doses of a pharmaceutical solution, and more specifically to preparing multiple doses of ranibizumab from a single-dose vial.

Opthalmic solution, such as ranibizumab is available from the manufacturer in a single-dose vial intended to be used one time per procedure. The drug is supplied with a tuberculin syringe, 30G needle, and a filter needle to extract it from the vial, which contains 0.26 ml of ranibizumab by volume. However, due to the dead space in the tuberculin syringe, a significant portion of the drug is unused and wasted.

ASPECTS OF THE INVENTION

The present disclosure is directed to various aspects of the present invention.

One aspect of the present invention is to provide a method which eliminates or significantly reduces wastage of a pharmaceutical solution, suspension, mixture, composition, or the like in any form (collectively "solution").

Another aspect of the present invention is to provide a method which prepares multiple sterile, stable and effective doses of a pharmaceutical solution from a single-dose.

Another aspect of the present invention is to provide a method which prepares multiple sterile, stable and effective doses of an ophthalmic solution from a single-dose.

Another aspect of the present invention is to provide a method which prepares multiple doses of ranibizumab from a single-use vial that are sterile, stable and effective for upto three months after refrigeration. In particular, the present invention utilizes a sterile procedure to extract multiple 0.5 mg/0.05 ml ranibizumab doses from a singe-use vial that are sterile, stable and effective. The procedure, by minimizing the dead space and decapping the vial, produces multiple doses.

Another aspect of the present invention is to provide a method which significantly reduces the cost of treatment for wet age-related macular degeneration (AMD).

Another aspect of the present invention is to provide a method which provides a retinal specialist or other medical professional with a prefilled syringe with a 31G needle that causes less pain than the manufacturer provided 30G needle.

BRIEF DESCRIPTION OF THE DRAWINGS

One of the above and other aspects, novel features and advantages of the present invention will become apparent from the following detailed description of the preferred embodiment(s) invention, as illustrated in the drawings, in which.

DETAILED DESCRIPTION OF THE PREFERRED EMBODIMENT(S) OF THE INVENTION

The present invention is based, in part, on the discovery that due to the dead space in a syringe, particularly a tuberculin syringe, a significant portion of the drug is unused and wasted. In particular, the present inventors discovered that ranibizumab is supplied by the manufacturer in a single-dose vial with a 30G needle and a filter needle. However, due to the dead space, much of the drug is not used is therefore wasted. The present invention provides an extraction method which produces multiple doses of ranibizumab from a single-dose vial. The doses produced are sterile, stable and effective for up to three months, less painful to the patient, and easier to use by a retinal specialist. The method described herein is not limited to ranibizumab and can be used for other drugs that have established stability under these condistions such as bevacizumab.

The following is a preferred embodiment for carrying out the method of the present invention.

Figure 1:
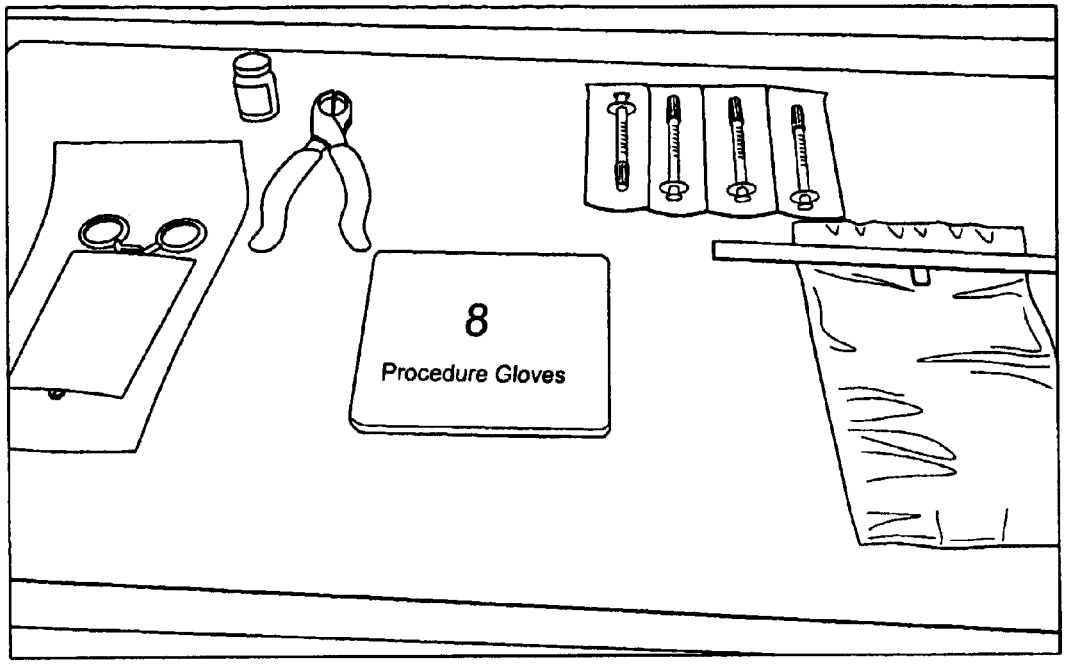
FIG. 1 illustrates the supplies for carrying out a preferred embodiment of the method of the invention.

Supply List (FIG. 1).

Sterile field (18"×26") by Busse Ref No. 696.

Sterile surgical gloves —one pair for the preparer and one for the assistant.

Four unopened, individually contained, sterile Monoject 0.3 ml 31 G 5/16 inch insulin syringes per vial of ranibizumab. NDC 08881609331; McK #1980101.

One vial of ranibizumab.

One 13 mm, or 13 mm/20 mm dual action vial decapper —available from Health Care Logistics item #7773.

Four sterile Whirl-Pak plastic bags per vial of ranibizumab. Bags may be obtained from Taylor Scientific (314) 962-5555; item #10-1695-06.

Sterile forceps.

Sterile hemostat.

Laminar or vertical airflow hood.

Sterile Field and Setup

Figure 2:
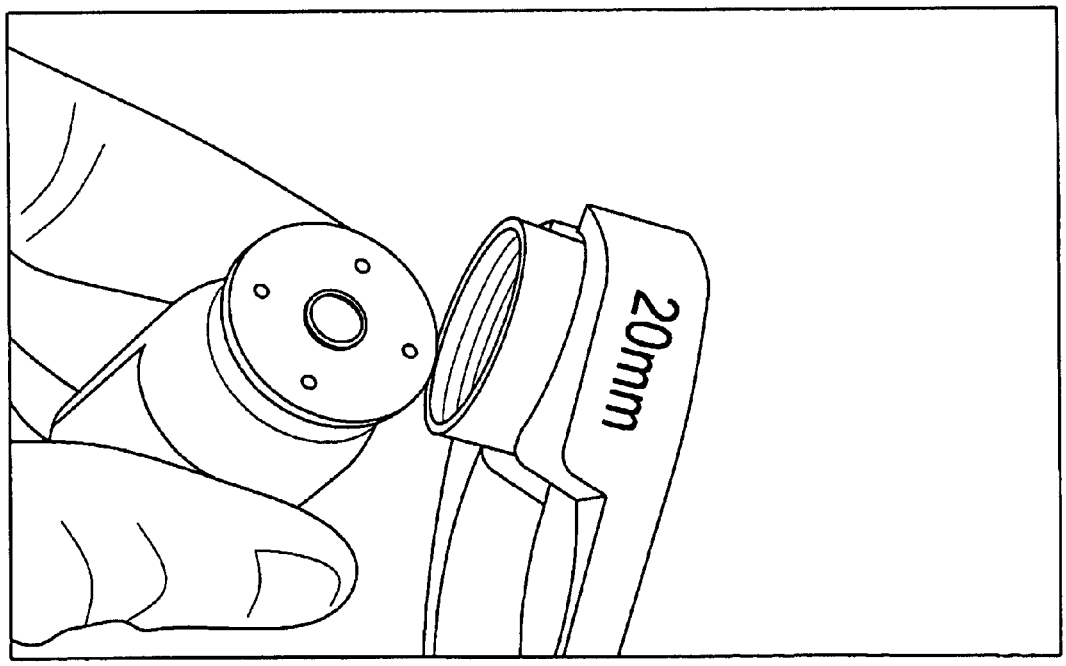
FIG. 2 illustrates an uncapping step of the preferred method of the present invention.

1. Aseptically prepare area according to USP 797 procedures in a clean laminar or vertical airflow hood.
2. Preparer and assistant wash hands.
3. Preparer applies sterile gloves using sterile technique.
4. Assistant opens sterile field package for preparer, who places it in laminar hood without contaminating gloves.
5. Assistant opens each sterile insulin syringe onto sterile field using sterile technique.
6. Assistant removes plastic cap of ranibizumab.
7. After properly applying alcohol to ranibizumab vial, the assistant removes metal top with decapper without removing the rubber stopper (FIG. 2).

8. Assistant rewashes hands, and applies sterile gloves inside hood.

Figure 3:
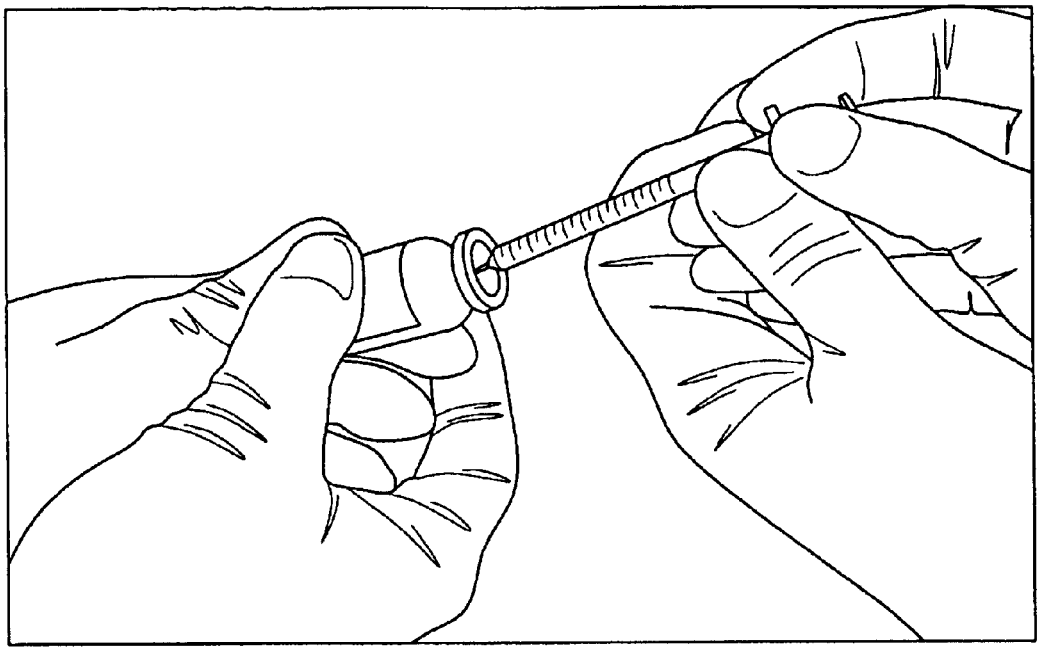
FIG. 3 illustrates an extraction step of the preferred method of the present invention.

Dose Extraction (FIG. 3).

Figure 4:
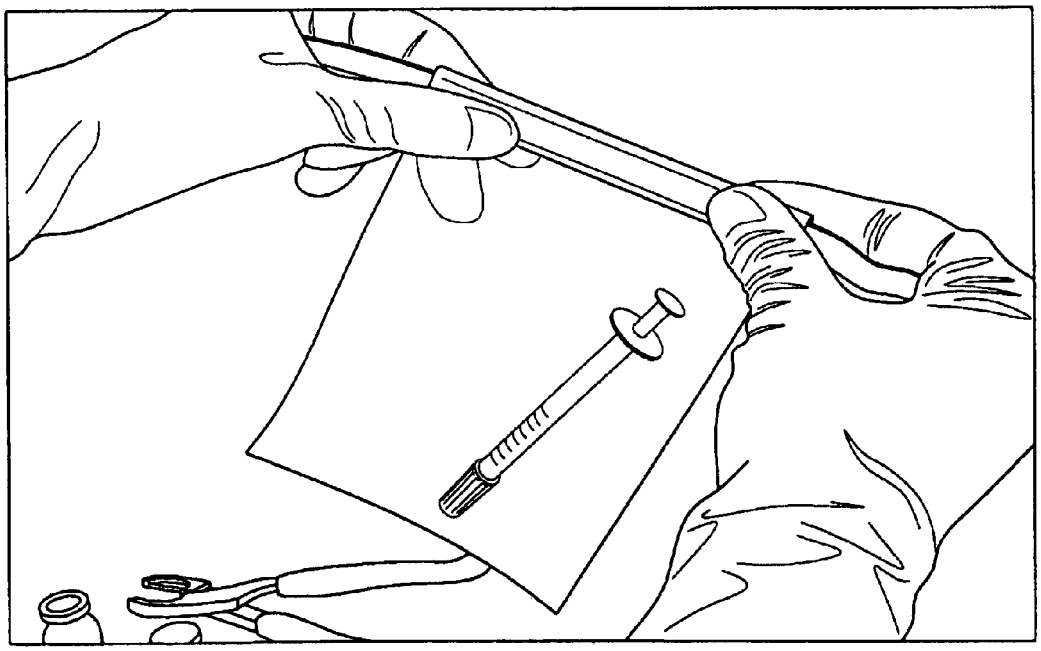
FIG. 4 illustrates placing of the extracted doses into sterile bags for refrigeration and later use.

1. Assistant removes rubber top of ranibizumab vial using sterile forceps without contaminating top of vial.
2. Assistant holds uncapped ranibizumab vial steady, while preparer inserts the insulin syringe needle inside without touching any part of the needle to the outside of the vial. In order to prevent dulling, it is important not to touch the needle to the bottom of the glass vial. If the needle touches anything but the drug inside vial, discard syringe and use another syringe.
3. Preparer withdraws ranibizumab to the 0.05 ml (5 unit) mark of the U-100 insulin syringe.
4. Preparer caps the insulin syringe and sets aside.
5. Repeat steps 2 to 4 to get the second, third and fourth doses.
6. If a bubble is visible, invert the syringe with the needle pointing upwards, tap the syringe gently until the bubble rises to the top, pull back the plunger slightly and push upwards until the bubbles disappear and the needle is primed.
7. Assistant opens sterile plastic bag and preparer places each syringe inside with needle facing down (FIG. 4). Assistant seals the plastic bag and removes from the hood.
8. Assistant affixes patient label to each bag with 60 day expiration date from time of preparation.

Sterility Testing

1. Draw remaining volume in vial into syringe and test for sterility using tryptic soy agar plates.
2. Disperse the drug onto the culture medium by spreading the sample over the agar surface by tilting and rotating the plate. Do not streak the plate.
3. Air dry plate until the liquid has evaporated.
4. Send inoculated plates to laboratory.

Stability Testing

1. Dilute assays with StabilCoat reagent.
2. Detect bound ranibizumab with goat anti-hIgG/F(ab') 2 antibody labeled with horseradish peroxidase.
3. Aliquot diluted detection antibody onto the VEGF plate at 100 μL/well, incubate and agitate.
4. Trigger chemiluminescent signal using the luminol-based SuperSignal ELISA Pic substrate.
5. The assay was performed by the Mayo Clinic College of Medicine, Clinical Immunology Laboratory, Rochester, Minn.

Lucentis Immunoassay Protocol

Lucentis concentrations were measured using an immunoassay technique as previously described (Ref. 5). Briefly, human recombinant VEGF-165 (R&D Systems, Minneapolis, Minn.) was immobilized on Microlite 2 (Thermo Labsystems, Franklin, Mass.) high-binding plates. The VEGF was diluted to a concentration of 1.0 μg/mL in a 50 mM carbonate buffer, PH 9, then aliquotted onto the Microlite plates at 100 μL/well. Following an overnight incubation at 4° C., the plates were washed 3 times with 1X phosphate-buffered saline (PBS) and then blocked for 4 hours at 4° C. with 1% bovine serum albumin in 1X PBS. After 3 washes with 1X PBS, the plates were stored dry at 4° C.

Samples to be assayed for stability were diluted StabilCoat reagent (Surmodics, Inc., Eden Prairie, Minn.) so as to be within the linear range of the assay. Samples were then aliquotted onto a VEGF plate at 100 μL/well and incubated for 2 hours at room temperature with agitation. For each individual assay, a standard curve was included using ranibizumab of known concentrations. After the initial incubation, the plates were washed 3 times with 1X PBS, 0.05% Tween-20. The bound ranibizumab was detected with a goat anti-hIgG/F(ab')$_2$ antibody labeled with horseradish peroxidase (Pierce Biotechnology Inc., Rockford, Ill.) diluted at 1:20,000 in Stabilcoat reagent. The diluted detection antibody was aliquotted onto the VEGF plate at 100 μL/well and incubated for 45 minutes at room temperature with agitation. Following this incubation, the plate was washed 3 times with 1X PBS. 0.05% Tween-20. The chemiluminescent signal was triggered using the luminol-based SuperSignal ELISA Pico Chemiluminescent Substrate (Pierce Biotechnology Inc.) according to the manufacturer's instructions.

Sterility in Syringe

Testing for bacterial growth at 37° C. in 73 syringes over a period of 1 to 60 days demonstrated sterility. No bacterial growth was detected.

Stability in Syringe

Figure 5:
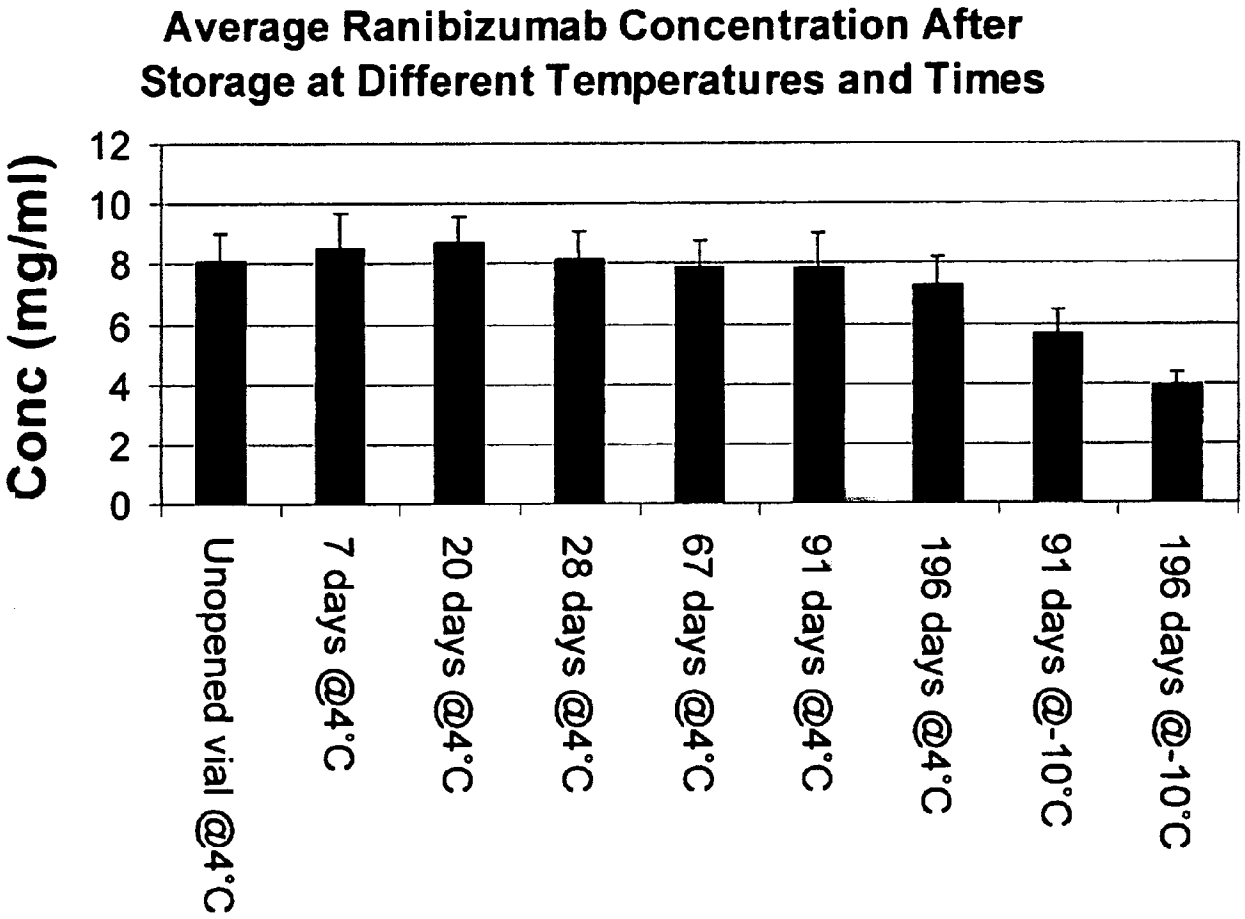
FIG. 5 is a bar chart illustrating stability of Lucentis® (raanibizumab) in various samples.

Multiple dose extraction or splitting from a single-use ranibizumab vial into syringes was found to be safe and the doses stable for upto three months under refrigeration (see FIG. 5 and Tables 5 & 7 ).

TABLE 1

Similar Drug Cost Comparison Estimate

| Drug | Price/dispense unit | Dose | Cost/dose | Cost/Year/Pt |
|---|---|---|---|---|
| Ranibizumab (Lucentis ®, Genentech, Inc.) | $1,450 per vial (1 dose/vial) | 0.5 mg intravitreally every 4 weeks | $1,450 | $17,400 |
| Pegaptanib* (Macugen ®, Pfizer, Inc.) | $760 per syringe (1 dose/syr) | 0.3 mg intravitreally every 6 weeks | $507 | $6,080 |
| Bevacizumabl (Avastin ® Genentech, Inc.) | $391 per vial (~25 doses per vial)* | 1.25 mg intravitreally every 4 weeks | $25-400 | $300-$4,800 |

TABLE 2

Total VISN (Veterans Integrated Service Network) 21 Drug Cost Estimate (n = 572 pts)

| Drug and Dose | Treat 20% × 1 yr | Treat 50% × 1 yr | Treat 90% × 1 yr |
|---|---|---|---|
| Ranibizumab 0.3 mg Q4wk $725/dose | $8,700 × 114 pts = $995,280 | $8,700 × 286 pts = $2,488,200 | $8,700 × 515 pts = $4,480,500 |
| Ranibizumab 0.5 mg Q4wk $1,450/dose | $17,400 × 114 pts = $1,990,560 | $17,400 × 286 pts = $4,976,400 | $17,400 × 515 pts = $8,961,000 |
| Ranibizumab 0.3 mg monthly × then Q3 months, 7 doses/yr @ $725/dose | $5,075 × 114 pts = $580,580 | $5,075 × 286 pts = $1,451,450 | $5,075 × 515 pts = $2,613,625 |
| Pegaptanib 0.3 mg Q6wk $507/dose | $6,080 × 114 pts = $695,552 | $6,080 × 286 pts = $1,738,880 | $6,080 × 515 pts = $3,131,200 |
| Bevacizumab 1.25 mg Q4wk $25-$400/dose | $300-$4,800 × 114 = $34,320-$549,120 | $300-$4,800 × 286 = $85,800-$1,372,800 | $300-$4,800 × 515 = $154,500-$2,472,000 |

TABLE 3

VISN (Veterans Integrated Service Network)
21 Cost Impact Estimate Based on Current Use

| Site | Pts | Doses | Cost | days w/2-4 doses | days w/>4 doses | Vials Avoid | Potential $ Avoid | Vials if appt is ±1 day | Add'l $ Avoid | Tot $ Avoid |
|---|---|---|---|---|---|---|---|---|---|---|
| VANC | 46 | 121 | $177K | 25 | 6 | 63 | $92K | 13 | $19K | $111K |
| VAPA | 27 | 73 | $107K | 15 | 5 | 34 | $50K | 6 | $9K | $58K |
| VASF | 15 | 34 | $50K | 4 | 0 | 5 | $7K | 7 | $10K | $18K |
| 6 Mon Total | 88 | 228 | $333K | 44 | 11 | 102 | $149K | 26 | $38K | $187K |
| 1 Yr Total | 176 | 456 | $666K | 88 | 22 | 204 | $298K | 52 | $76K | $374K |

COST SAVINGS

TABLE 4A $405,000 REAL VETERANS AFFAIRS SAVINGS
(May 01, 2007 to Jul. 31, 2008)

| Ranibizumab Lucentis ® 0.5 mg | #Doses | #Eyes Treated | # Treated Patients | Veterans Contract Cost |
|---|---|---|---|---|
| Standard Technique | 389 | 105 | 96 | $540,000 |
| Splitting Technique | 389 | 105 | 96 | $135,000 |

TABLE 4B $6.59 BILLION ESTIMATED SAVINGS PER YEAR

| Ranibizumab (Lucentis ®) 0.5 mg | Treat 10% Cost[2] (Billion) | Treat 25% Cost[2] (Billion) | Treat 75% Cost[2] (Billion) |
|---|---|---|---|
| Standard Technique $9750/pt/yr | $1.17 | $2.93 | $8.78 |
| Splitting Technique $2438/pt/yr | $0.30 | $0.74 | $2.19 |
| Cost Savings/yr | $0.87 | $2.19 | $6.59 |

Estimated U.S.A. Drug Costs: n = 1.2 million patients with neovascular AMD[1] each receiving 4 doses/year.
[1]The Eye Diseases Prevalence Research Group Arch Ophthalmol. 2004; 122:564-572.
[2]Average Wholesale Price of Ranibizumab is $2438 per vial.

Figure 6:
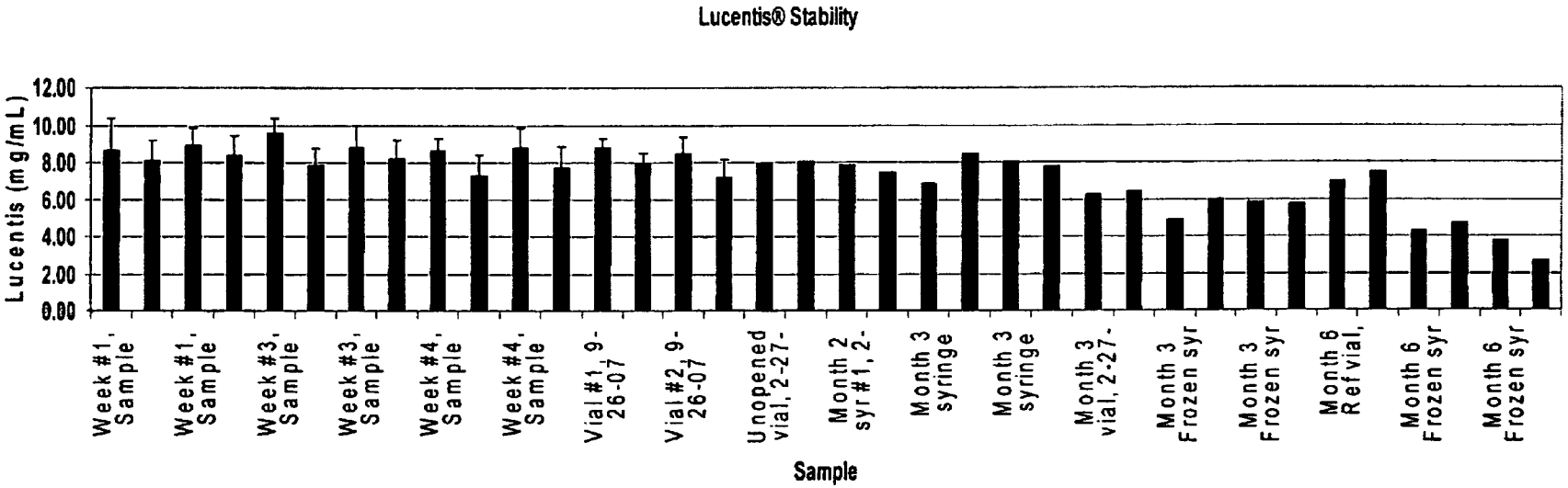
FIG. 6 is a bar chart illustrating average ranibizumab concentration after storage at different temperatures and times, showing stability of the split doses for upto three months after refrigeration.

The following Table 5 corresponds to FIG. 6 and provides stability data for ranibizumab in various samples over a six-month period.

TABLE 5

| | | Average Concentration (mg/mL) | SD | |
|---|---|---|---|---|
| Week 1 | Week #1, Sample #1, Sep. 26, 2007 | 8.65 | 1.73 | avg wk 1 (syr) 8.53 +/− 1.17 |
| | Week #1, Sample #1, Sep. 27, 2007 | 8.15 | 1.03 | |
| | Week #1, Sample #2, Sep. 26, 2007 | 8.93 | 0.90 | |
| | Week #1, Sample #2, Sep. 27, 2007 | 8.39 | 1.03 | |
| Week 3 | Week #3, Sample #1, Sep. 26, 2007 | 9.62 | 0.76 | Avg wk 3 (syr) 8.68 +/− 0.89 |

TABLE 5-continued

| | | Average Concentration (mg/mL) | SD | |
|---|---|---|---|---|
| | Week #3, Sample #1, Sep. 27, 2007 | 7.93 | 0.84 | |
| | Week #3, Sample #2, Sep. 26, 2007 | 8.88 | 1.04 | |
| | Week #3, Sample #2, Sep. 27, 2007 | 8.29 | 0.90 | |
| Week 4 | Week #4, Sample #1, Sep. 26, 2007 | 8.65 | 0.61 | Avg wk 4 (syr) 8.14 +/− 0.96 |
| | Week #4, Sample #1, Sep. 27, 2007 | 7.30 | 1.10 | |
| | Week #4, Sample #2, Sep. 26, 2007 | 8.89 | 0.97 | |
| | Week #4, Sample #2, Sep. 27, 2007 | 7.71 | 1.14 | |
| | Vial #1, Sep. 26, 2007 | 8.87 | 0.39 | Avg 4 wk (vial) 8.45 +/− 0.43 |
| | Vial #1, Sep. 27, 2007 | 8.02 | 0.47 | |
| | Vial #2, Sep. 26, 2007 | 8.50 | 0.89 | Avg 1 wk (vial) 7.89 +/− 0.9 |
| | Vial #2, Sep. 27, 2007 | 7.27 | 0.91 | |
| | Unopened vial, Feb. 27, 2008 | 8.01 | 0.71 | 8.9% |
| | Unopened vial, Feb. 28, 2008 | 8.11 | 1.19 | 14.7% |
| Month 2 | Refrigerated syringe, Feb. 27, 2008 | 7.89 | 0.86 | 10.9% |
| | Refrigerated syringe, Feb. 28, 2008 | 7.47 | 0.35 | 4.7% |
| Month 3 | Refrigerated syringe #1, Feb. 27, 2008 | 6.89 | 0.75 | 10.9% |
| | Refrigerated syringe #1, Feb. 28, 2008 | 8.52 | 0.85 | 10.0% |
| | Refrigerated syringe #2, Feb. 27, 2008 | 8.06 | 1.12 | 13.9% |
| | Refrigerated syringe #2 Feb. 28, 2008 | 7.85 | 2.13 | 27.1% |
| | Refrigerated vial, Feb. 27, 2008 | 6.27 | 1.27 | 20.3% |
| | Refrigerated vial, Feb. 28, 2008 | 6.46 | 1.44 | 22.3% |
| | Frozen syringe #1, Feb. 27, 2008 | 4.97 | 0.47 | 9.5% |
| | Frozen syringe #1, Feb. 28, 2008 | 6.07 | 0.87 | 14.3% |
| | Frozen syringe | 5.87 | 0.93 | 15.8% |

TABLE 5-continued

| | | Average Concentration (mg/mL) | SD | |
|---|---|---|---|---|
| | #2, Feb. 27, 2008 Frozen syringe #2, Feb. 28, 2008 | 5.78 | 0.94 | 16.3% |
| Month 6 | Refrigerated vial, Feb. 27, 2008 | 7.02 | 0.71 | 10.1% |
| | Refrigerated vial, Feb. 28, 2008 | 7.47 | 1.19 | 15.9% |
| | Frozen syringe #1, Feb. 27, 2008 | 4.30 | 0.31 | 7.2% |
| | Frozen syringe #1, Feb. 28, 2008 | 4.76 | 0.51 | 10.7% |
| | Frozen syringe #2, Feb. 27, 2008 | 3.82 | 0.37 | 9.7% |
| | Frozen syringe #2, Feb. 28, 2008 | 2.72 | 0.63 | 23.2% |

The following Tables 7 and 8 correspond to FIG. 5 and provide data for average ranibizumab concentration after storage at different temperatures and times.

TABLE 7

| | Average Concentration (mg/mL) | SD |
|---|---|---|
| Unopened vial @4° C. | 8.06 | 0.95 |
| 7 days @4° C. | 8.53 | 1.17 |
| 20 days @4° C. | 8.68 | 0.89 |
| 28 days @4° C. | 8.14 | 0.96 |
| 67 days @4° C. | 7.89 | 0.86 |
| 91 days @4° C. | 7.83 | 1.21 |
| 196 days @4° C. | 7.25 | 0.95 |
| 91 days @−10° C. | 5.67 | 0.80 |
| 196 days @−10° C. | 3.90 | 0.46 |

TABLE 8

| Statistics (t-test) | |
|---|---|
| Storage Time & Temperature | P Value |
| 7 days @ 4° C. | 0.210 |
| 20 days @ 4° C. | 0.277 |
| 28 days @ 4° C. | 0.899 |
| 67 days @ 4° C. | 0.151 |
| 91 days @ 4° C. | 0.382 |
| 196 days @ 4° C. | 0.032 |
| 91 days @ −10° C. | <0.001 |
| 196 days @ −10° C. | <0.001 |

TABLE 9

| Adverse Reactions 0 CASES OF ENDOPHTHALMITIS | | | | |
|---|---|---|---|---|
| Increased BP | Increased IOP | Abrasion/ Irritation | Other | Total # ADR |
| 1 (0.3%) | 1 (0.3%) | 5 (1.3%) | 2 (0.5%) | 9 (2.3%) |

Reported May 1, 2007 to Jul. 31, 2008.
(n = 96 pts; 105 eyes; 389 injections).

Summary of main advantages of the present invention.

Using vial decapping technique and taking advantage of reduced syringe dead-space with 31 G, 5/16 inch needles, consistently produces 4 doses per vial.

Syringe sterility testing on each batch found no bacterial growth.

Ranibizumab was found to be stable in syringes for up to 3 months at 4° C.

No serious complications were found in 389 doses.

Incidence of minor adverse reactions was 2.3% which is similar to that seen with standard injection technique.

Conclusion

Multiple dose extraction from ranibizumab vials into syringes is safe and the product is stable.

Drug costs are reduced by 75% .

Minimal drug wastage since ranibizumab stable in syringes for up to 3 months under refrigeration.

Smaller gauge needle and shorter needle length make ranibizumab injection more comfortable for the patient and easier for the surgeon.

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

REFERENCES

The following references, including any cited in the disclosure herein, are hereby incorporated herein in their entirety by reference.

1. USP Chapter 797 Pharmaceutical Compounding: Sterile Preparations.
2. VISN 21, Aseptic Ranibizumab (Lucentis®) Dose Preparation Procedure.
3 . VISN 21 Criteria for non-formulary use of ranibizumab injection.
4. National PBM Drug Monograph for Ranibizumab (Lucentis®).
5. Bakri S J, Snyder M R, Reid J M, Pulido J S Ezzat M K, Singh R J. Pharmacokinetics of intravitreal ranibizumab (Lucentis). Ophthalmology, 114 (2007) 2179-2182.

What is claimed is:

1. A method of preparing a plurality of doses of a pharmaceutical solution from a single-dose container, comprising the steps of:

a) providing a sterile enclosed area with a plurality of unused sterile syringes, a decapper, and a plurality of sterile bags;

b) opening a single-use container of a pharmaceutical solution in the enclosed area;

c) withdrawing a first portion of the pharmaceutical solution using one of the sterile syringes;

d) withdrawing a second portion of the pharmaceutical solution using a second of the sterile syringes;

e) repeating step d) for the remaining pharmaceutical solution using the remaining sterile syringes; and f) placing the sterile syringes containing portions of the pharmaceutical solution individually in the sterile bags.

2. The method of claim 1, wherein:

steps c) and d) are performed while the single-use container is held steady.

3. The method of claim 1, wherein:

steps c) and d) are performed by one person while the single-use container is held steady by another person.

4. The method of claim 2, wherein:

steps c) and d) are performed without contacting the container with the syringe needle.

5. The method of claim 1, wherein;

step c) comprises withdrawing 0.05 ml of the pharmaceutical solution.

6. The method of claim 1, wherein:

step c) or d) comprises withdrawing a supplemental portion of the pharmaceutical solution if a bubble appears in the withdrawn solution.

7. The method of claim 6, wherein:

step c) and d) comprise withdrawing 0.05 ml of the pharmaceutical solution.

8. The method of claim 7, wherein:

the supplemental portion comprises withdrawing 0.005 ml of the pharmaceutical solution.

9. The method of claim 1, wherein:

the pharmaceutical solution comprises about 0.26 ml of an ophthalmic drug provided in a vial.

10. The method of claim 9, wherein:

the drug comprises ranibizumab.

11. The method of claim 9, wherein:

the method prepares four individual doses of about 0.05 ml each of the ophthalmic drug.

12. The method of claim 1, wherein:

the sterile enclosed area comprises a laminar or vertical airflow hood.

13. A method of preparing a plurality of individual doses of an ophthalmic solution from a single-dose vial, comprising the steps of:

a) providing a sterile enclosed hood with a plurality of unused sterile syringes, a vial decapper, and a plurality of sterile bags;

b) opening a single-use vial containing about 0.26 ml of an ophthalmic solution in the hood;

c) withdrawing about 0.05 ml of the ophthalmic solution using one of the sterile syringes;

d) withdrawing about 0.05 ml of the ophthalmic solution using a second of the sterile syringes;

e) repeating step d) for the remaining ophthalmic solution using the remaining syringes; and f) placing the sterile syringes each containing about 0.05 ml of the ophthalmic solution individually in the sterile bags.

14. The method of claim 13, wherein:

steps c) and d) comprise withdrawing an additional 0.005 ml of the ophthalmic solution if a bubble appears in the withdrawn solution.

15. The method of claim 13, wherein:

steps c) and d) are performed without contacting the vial with the syringes needle.

16. The method of claim 13, wherein:

the ophthalmic solution comprises ranibizumab.

17. The method of claim 16, wherein:

the method prepares four individual doses of about 0.05 ml each of ranibizumab solution.

* * * * *